United States Patent [19]
Marsili et al.

[11] 3,963,705
[45] June 15, 1976

[54] PROCESS FOR THE PREPARATION OF 3-IMINOMETHYL DERIVATIVES OF RIFAMYCIN SV

[75] Inventors: Leonardo Marsili; Carmine Pasqualucci, both of Milan, Italy

[73] Assignee: Archifar Industrie Chimiche del Trentino S.p.A., Rovereto, Italy

[22] Filed: May 23, 1974

[21] Appl. No.: 472,887

[30] Foreign Application Priority Data
July 25, 1973 Italy .................................. 27066/73
Jan. 24, 1974 Italy .................................. 19774/74

[52] U.S. Cl. .......................... 260/239.3 P; 424/244; 424/248
[51] Int. Cl.² ........................................ C07D 498/04
[58] Field of Search ............................. 260/239.3 P

[56] References Cited
UNITED STATES PATENTS
3,342,810   9/1967   Maggi et al .................. 260/239.3 P

*Primary Examiner*—John M. Ford
*Assistant Examiner*—Robert T. Bond
*Attorney, Agent, or Firm*—Haseltine, Lake & Waters

[57] ABSTRACT

A process for the preparation in homogeneous phase and in quantitative yield of 3-iminomethyl derivatives of rifamycin SV useful as antibiotic agents. Rifamycin S is reacted in an organic solvent to give a solution of 1,3-oxazino-(5,6-c) rifamycins which is treated with an organic solvent at a pH from 4 to 6. The aqueous phase is discharged and the organic phase is treated with an amine under basic conditions, the desired derivatives being finally isolated from this organic phase according to usual techniques.

10 Claims, No Drawings

PROCESS FOR THE PREPARATION OF 3-IMINOMETHYL DERIVATIVES OF RIFAMYCIN SV

The present invention is concerned with a process for the preparation of 3-iminomethyl derivatives of rifamycin SV useful as antibiotic agents. The French Pat. No. 1,457,435 describes 3-iminomethyl derivatives of rifamycin SV characterized by the following general formula

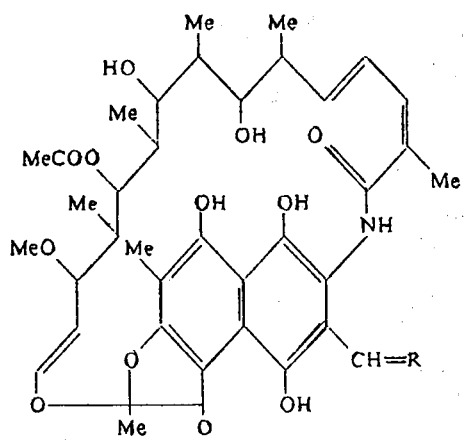

(I)

wherein R is oxygen, H(OH), dialkoxy, imino, substituted imino, hydrazono and substituted hydrazono, which are antibiotic substances very active against pathogenic bacteria. A representative compound of this series is the 3-(4-methyl-piperazin-1-yl)-iminomethyl-rifamycin SV, a substituted hydrazone derivative of 3-formyl-rifamycin SV known with its International Non-proprietary Name "rifampicin".

According to the above patent, the compounds of formula (I) above are obtained by subjecting a Mannich base of rifamycin SV to an oxidation reaction and hydrolysing the Schiff base thus obtained to the 3-formyl-rifamycin SV (formula (I), R = oxygen).

The latter can be transformed into its acetals (formula (I), R = dialkoxy), reduced to form the corresponding alcohol (formula (I), R = H(OH) ) or reacted with primary amines (formula (I), R = substituted imino) or hydrazines (formula (I), R = substituted hydrazono).

French Pat. No. 1,585,041 describes an improved method for the preparation of the 3-hydrazonomethyl derivatives of rifamycin SV of formula (I) above which comprises treating rifamycin S of formula

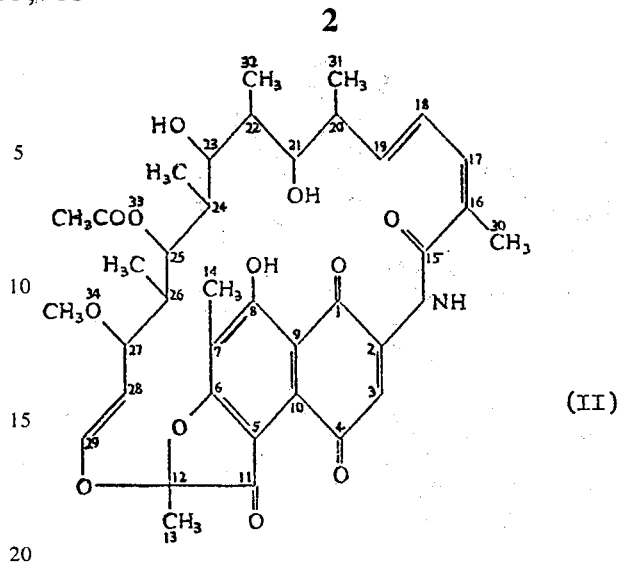

(II)

with formaldehyde and a suitable primary amine, preferably tert.butylamine, or with an aldimino derivative obtained from equimolecular amounts of said primary amine and of formaldehyde in the presence of an oxidizing agent, preferably manganese dioxide, then treating the intermediate compound thus obtained with about 2 molar equivalents of the desired hydrazine in order to accomplish both the reduction and the transimination and finally isolating the compound of formula (I) above, in which R represents hydrazono group, by separating the final product from its salt with the primary amine, preferably with tert.butylamine. The preparation of the hydrazonomethyl derivatives starting from rifamycin S according to the French Pat. No. 1,585,041 thus involves a five-steps process comprising a condensation to a Mannich base, an oxidation to a Schiff base, a reduction to the hydroquinone-type compound, a trans-imination and a hydrolysis.

In particular the intermediate compound obtained from rifamycin S must be subjected to a reduction with ascorbic acid before the trans-imination in order to convert the quinone-like compound into the corresponding hydroquinone-like derivative. The use of ascorbic acid may be avoided by carrying out the trans-imination with at least about 2 molar equivalents of the hydrazine, the second molar equivalent acting as a reducing agent. In any case, there is obtained a salt of the final compound with the employed amine, which precipitates and from which the desired final compound must be isolated by hydrolysis.

The main object of the present invention is to have a process by which it is possible to obtain 3-iminomethyl derivatives of rifamycin SV in quantitative yield, the process being carried out in two steps only and in a very short time and requiring the use of low cost reagents.

Said objects and still other object are obtained by a process which comprises reacting rifamycin S of formula

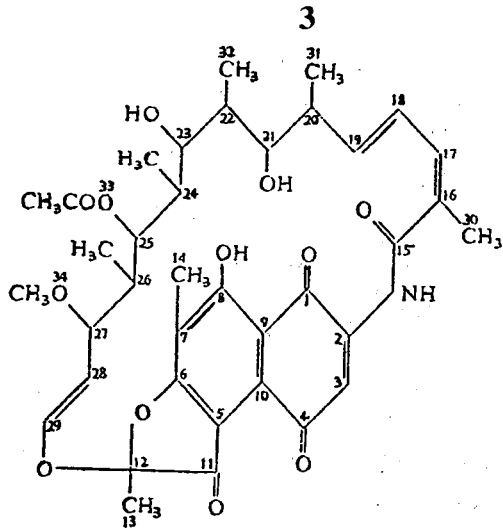

(II)

with a compound of formula

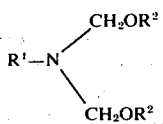

(V)

in which $R^1$ is lower alkyl, lower alkenyl, cycloalkyl of from 5 to 6 carbon atoms, phenyl, benzyl or $\alpha$ or $\beta$ or $\beta$-phenethyl and $R^2$ is hydrogen or lower alkyl, in a first inert organic solvent at a temperature ranging from 0°C to the boiling temperature of the solvent employed to give a solution of 1,3-oxazino (5,6-c) rifamycins of formula

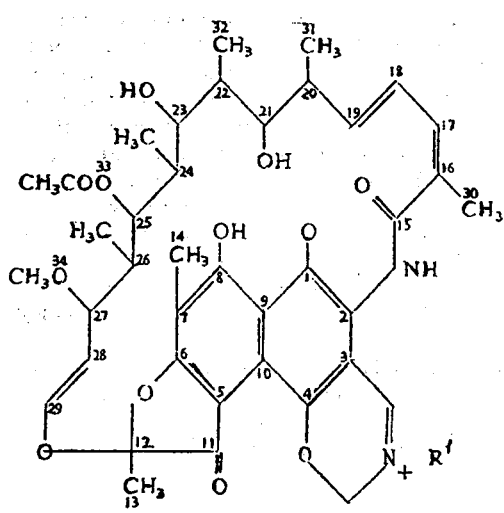

(IV)

in which $R^1$ is as above defined, treating said solution with water and a second inert organic solvent immiscible with water at a pH adjusted at a value from 4 to 6, then discharging the aqueous phase and treating the organic phase with a primary amine, hydrazine, mono-substituted hydrazine or asymmetric di-substituted hydrazine at a temperature from about 20°C to about 80°C under basic conditions, 3-iminomethyl derivatives of rifamycin SV of formula

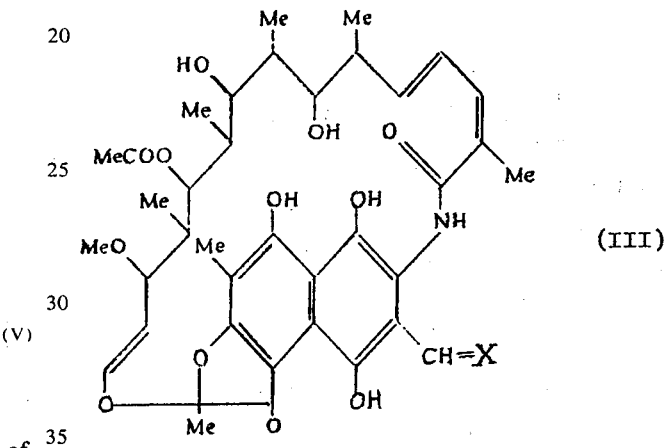

(III)

being isolated from this solution according to usual techniques.

If the first solvent is mixible with water the compound of formula (IV) precipitates and can be isolated. This compound of formula (IV) can be dissolved in an inert organic solvent and treated with a primary amine, hydrazine, mono-substituted hydrazine or asymmetric di-substituted hydrazine at a temperature from about 20°C to about 80°C under basic conditions, 3-iminomethyl derivatives of rifamycin SV of formula (III) being isolated from this solution according to usual techniques.

The compounds of formula (V) are prepared according to the procedure described in J.Chem.Soc. 123, 532, (1923).

The term "lower alkyl", as used herein, includes straight and branched saturated aliphatic hydrocarbon radicals containing from 1 to 6 carbon atoms such as methyl, ethyl, propyl, isopropyl, n-butyl, isobutyl, sec.-butyl, tert.butyl, n-pentyl, 2-methyl-butyl, n-hexyl, 2-methyl-pentyl. The term "lower alkenyl" includes ethylenically unsaturated aliphatic hydrocarbon radicals containing from 3 to 6 carbon atoms such as allyl, crotyl, methacryl, 3-pentenyl, 3-hexenyl.

The reaction temperature varies with the solvent employed. If a chlorinated solvent or in general a polar solvent is used, the reaction can be carried out at a relatively low temperature (20°–50°C), whereas, if a practically apolar solvent such as toluene is employed, it is preferable to operate at a higher temperature.

The reaction time depends upon the nature of the starting material employed and upon the temperature. Even though the reaction time can be prolonged up to 24 hours at 40°C and the reaction mixture can be allowed to stand at about 0°C for other 24 hours without observing any degradation of the rifamycin molecule, the conversion of the 1,3-oxazino(5,6-c)rifamycins of formula (IV) above into the 3-iminomethyl derivatives of formula (III) is practically immediate in the interval of temperature given above (20°–80°C). In general, under these conditions the reaction time varies between few minutes and a maximum of 3 hours.

The primary amine, hydrazine, mono-substituted hydrazine or asymmetric di-substituted hydrazine is employed in an amount preferably ranging between about the stoichiometrical amount and an excess of 4–5 moles of the primary amine, hydrazine, mono-substituted hydrazine or asymmetric di-substituted hydrazine per mole of starting compound (IV).

Exemplary amines or hydrazines which can react with the 1,3-oxazino (5,6-c)rifamycins of formula (IV) above to give corresponding 3-iminomethyl derivatives of formula (III) are benzyl-amine, $\alpha$ - or $\beta$ -phenethylamine, aniline, o-toluidine, m-toluidine, p-toluidine, 2,6-lutidine, p-chloraniline, 2-naphthylamine, 2-aminopyridine, 4-amino-pyridine, hydrazine, benzylhydrazine, phenylhydrazine, 1-amino-pyrrolidine, 1-aminopiperidine, 4-amino-morpholine and 1-amino-4-methyl-piperazine which last, according to the present invention, gives rifampicin.

The basic conditions under which the reaction is carried out are obtained either by using an excess (up to about 4–5 moles) of the primary amine, hydrazine, mono-substituted hydrazine or asymmetric di-substituted hydrazine or by using in the reaction medium a secondary or tertiary amine such as pyrrolidine, trimethylamine, triethylamine, 1-methylpyrrolidine. The method according to which at the end of the reaction the 3-iminomethyl derivatives of formula (III) are isolated preferably includes adjusting the pH of the reaction mixture to slight acid values, washing with water to eliminate the excess of the salified organic base, concentrating the reaction mixture and taking up with a suitable solvent. Thus, the 3-iminomethyl derivatives of rifamycin SV are directly obtained from compound (IV) in practically quantitative yield.

Even though any 1,3-oxazino (5,6-c) rifamycin of formula (IV) above can be converted into the 3-iminomethyl derivatives of formula (III), the best yields and the shortest reaction times are obtained by using an 1,3 oxazino (5,6-c)rifamycin of formula (IV), where $R^1$ is lower alkyl or lower alkenyl. In such a case, after 5 – 20 minutes the reaction is over and the compounds of formula (III) may be isolated in practically quantitative yield.

In order to make the features of the present invention clear, some examples of said process will now be given:

EXAMPLE 1

A mixture of 6.5 g. N,N-dihydroxymethyl-tert.butylamine, 13.9 g. rifamycin S and 40 ml. dimethylformamide is heated at 33°C under stirring for 60 minutes. The blue solution thus obtained is poured into 300 ml. of water acidified with 3 ml. of acetice acid and extracted with 200 ml. chloroform. To the organic phase there are added 5.5 g. pyrrolidine and 3 g. 1-amino-4-methylpiperazine and the mixture is stirred 40 minutes at 30°C. The reaction mixture is washed with water acidified with acetic acid up to pH 5 and then with water.

The organic phase is dried over sodium sulfate, filtered and concentrated to dryness to give 15.4 g. of a crude product which, by recrystallization from acetone, affords 13.2 g. of chromatografically pure rifampicin.

EXAMPLE 2

To a solution of 18 g. of rifamycin S dissolved in 65 ml. of dimethylsulfoxide in a 250 ml. four-necked flask, 10 ml. of di(isobutoxymethyl)-methylamine (formula V, $R^1 = CH_3$ , $R^2 =$ isobutyl) are added and the solution is heated for 5 minutes at 50°C. The blue solution thus obtained is diluted with a mixture of 375 ml. of water acidified with 6 ml. of acetic acid 96%, and extracted with 250 ml. of chloroform. The organic layer is separated and 5.5 g. of pyrrolidine and 4 g. of 1-amino-4-methyl-piperazine are added. The solution is heated 60 minutes at 40°C, then acidified to pH 5 with diluted acetic acid and washed with water. The organic phase is dried over sodium sulfate, filtered and concentrated to dryness. Recrystallization of the residue from acetone affords pure rifampicin in practically quantitative yield.

EXAMPLE 3

To a solution of 18 g. rifamycin S in 65 ml. dimethylsulfoxide, 10ml. diisobutoxymethyl-methylamine are added and the mixture is heated 5 minutes at 50°C, then poured into 375 ml. of distilled water acidified with 6 ml. of 96% acetic acid and extracted with 250 ml. chloroform. The organic phase is separated, treated with 11 g. triethylamine and 4 g. 1-amino-4-methyl-piperazine, then heated 24 hours at 40°C. By operating as described in Example 17, there are obtained 19.2 g. of a rifampicin showing an activity of 98.7%.

EXAMPLE 4

A solution of 6.5 g. of N,N dihydroxymethyl-tert.butylamine, 40 ml. of dimethylformamide and 13.9 g. of rifamycin S is stirred in a 100 ml. four-necked flask for 60 minutes at 33°C.

The reaction mixture is poured into 300 ml. of water acidified with 2 ml. of acetic acid. The obtained precipitate is filtered, washed with water and dried at 40°C, under vacuum.

Yield: 14.5 g. of N,-tert. butyl-1,3-oxazino (5,6-c) rifamycin.

EXAMPLE 5

A mixture of 2.8 g. of pyrrolidine and 1.38 g. of 1-amino-4-methyl-piperazine is added to a solution of 7.9 g. of N-tert.butyl-1,3-oxazino (5,6-c)rifamycin (prepared according to Example 4) in 30 ml. of tetrahydrofuran in a 100 ml. four-necked flask. After 20 minutes stirring at room temperature the reaction is over. The reaction mixture is dissolved in 100 ml. chloroform, acidified to pH 5 with diluted acetic acid and washed with water. The chloroformic phase is dried with sodium sulfate and, after filtration, the solvent is evaporated to give 8.2 g. of a crude product which, after recrystallization from acetone yields 7.2 g. of rifampicin as a unitary product on thin layer chromatography.

EXAMPLE 6

4 g. of benylamine are added to a solution of 7.9 g. of N-tert.butyl-1,3-oxazino (5,6-c) rifamycin (prepared according to Example 4) in 30 ml. of tetrahydrofuran and after 15 minutes stirring at 30°C the reaction is complete. The solution is diluted with 100 ml. of chloroform, acidified to pH 5 with diluted acetic acid, washed with water and dried over sodium sulfate. After filtration, the solvent is evaporated and the product is collected. There are obtained 7.8 g. of 3-benzyliminomethyl rifamycin SV (formula III, X=N—CH$_2$—C$_6$H$_5$). The U.V. spectrum shows an absorption max. at 555 mµ.

EXAMPLE 7

1.5 g. of hydrazine hydrate are added to a solution of 6 g. of N-tert.butyl-1,3-oxazino (5,6-c)rifamycin (prepared according to Example 4) in 30 ml. of tetrahydrofuran. After 5 minutes stirring at room temperature the reaction is complete. By operating as set forth in Example 5, 5.3 g. of the hydrazone of the 3-formyl-rifamycin SV (formula III, X=N—NH$_2$) are obtained.

The U.V. spectrum shows an absorption max. at 325 and 473 mµ.

EXAMPLE 8

13.9 g. of rifamycin S are dissolved in 40 ml. of dimethylacetamide, in a 100 ml. four-necked flask.

7 g. of N,N diisopropoxymethyl-allylamine are added and the solution is heated for 15 minutes at 70°C. The reaction mixture is poured into 300 ml. of water acidified with 2 ml. of acetic acid. The obtained precipitate is filtered, washed with water and dried at 40°C, under vacuum.

Yield: 14.3 g. of N-allyl-1,3-oxazino-(5,6-c)rifamycin.

EXAMPLE 9

A mixture of 2.9 g. of 1-methyl-pyrrolidine and 1.38 g. of 1-amino-4-methyl-piperazine is added to a solution of 7.8 g. of N-allyl-1,3-oxazino (5,6-c)rifamycin (prepared according to Example 8) in 40 ml. methylene chloride in a 100 ml. four-necked flask.

After 20 minutes stirring the reaction is over and the mixture is dissolved in 100 ml. chloroform, acidified to pH 5 with diluted acetic acid and washed with water. The chloroformic phase is dried over sodium sulfate, filtered, concentrated to dryness and recrystallized from acetone to give 7.2 g. of rifampicin as a pure product. Only one spot on T.L.C.

EXAMPLE 10

A mixture of 13.9 g. of rifamycin S, 6.5 g. of N,N dimethoxymethylcyclohexylamine and 4.0 ml. of dimethylsulfoxide is heated in a 100 ml. four-necked flask for 45 minutes at 50°C. The reaction mixture is poured into 300 ml. of water acidified with 2 ml. of acetic acid. The obtained precipitate is filtered, washed with water and dried at 40°C., under vacuum.

Yield: 15.3 of N-cyclohexyl-1,3-oxazino(5,6-c)rifamycin.

EXAMPLE 11

A solution of 3.1 g. of pyrrolidine in 5 ml. toluene in 10 minutes is added to a mixture of 7.1 g. of N-cyclohexyl-1,3-oxazino(5,6-c)rifamycin (prepared according to Example 10) 45 ml. of toluene and 1.2 g. of 1-amino-4-methyl-piperazine at 75°C.

After 10 minutes heating, the reaction mixture is cooled, taken up with 100 ml. chloroform, washed with water acidified with acetic acid and then with water. The dried organic phase is concentrated to dryness and the residue is recrystallized from acetone to give 5.8 g. of pure rifampicin.

EXAMPLE 12

13.9 g. of rifamycin S are dissolved in 40 ml. of hexamethylphosphorictriamide in a 100 ml. four-necked flask. 7.5 g. of N,N diethoxymethylbenzylamine are added and the solution is heated for 20 minutes at 60°C. The reaction mixture is poured into 400 ml. of water acidified with 2 ml. of acetic acid. The obtained precipitate is filtered, washed with water and dried at 40°C, under vacuum.

Yield: 15.8 g. of N-benzyl-1,3-oxazino(5,6-c)rifamycin.

EXAMPLE 13

A mixture of 2.9 g. of 1-methyl-pyrrolidine and 1.38 g. of 1-amino-4-methyl-piperazine is added to a solution of 8.3 g. of N-benzyl-1,3-oxazino (5,6-c)rifamycin (prepared according to Example 12) in 40 ml. methylene chloride in a 100 ml. four-necked flask.

After 20 minutes stirring the reaction is over and the mixture is dissolved in 100 ml. chloroform, acidified to pH 5 with diluted acetic acid and washed with water. The chloroformic phase is dried over sodium sulfate, filtered, concentrated to dryness and recrystallized from acetone to give 7.2 g. of rifampicin as a pure product. Only one spot on T.L.C.

EXAMPLE 14

14 g. of rifamycin S are dissolved in 40 ml. acetone in a 100 ml. four-necked flask. 5 g. of N,N diisobutoxymethyl-methylamine are added and the solution is stirred for 3 hours at 40°C. The reaction mixture is poured into 300 ml. of water acidified with 3 ml. of acetic acid. The obtained precipitate is filtered, washed with water and dried at 40°C, under vacuum.

Yield: 13.8 g. of crude product.

The crude product is mixed with 60 ml. of toluene in a 100 ml. flask; the mixture is stirred for 10 minutes at 60°C and then filtered.

Yield: 12.5 g. of N -methyl-1,3-oxazino(5,6-c)rifamycin.

EXAMPLE 15

A mixture of 14 g. of rifamycin S, 50 ml. of n-propyl alcohol and 5.5 g. of N,N diisobutoxymethyl-methylamine is stirred in a 100 ml. four-necked flask for 60 minutes at 60°C.

The reaction solution is poured into 500ml. of water acidified with 5 ml. of acetic acid. The obtained precipitate is filtered, washed with water and dried at 40°C, under vacuum.

Yield: 12.2 g. of crude product.

The crude product is dissolved in 100 ml. of chloroform and a mixture of 250 ml. of toluene and 750 ml. of petroleum ether is added. The obtained precipitate is filtered and dried at 40°C, under vacuum.

Yield: 4.2 g. of N-methyl-1,3-oxazino(5,6-c)rifamycin.

The product is identical to that described in example 14.

EXAMPLE 16

A solution of 3.1 g. of pyrrolidine in 5 ml. toluene in 10 minutes is added to a mixture of 6.5 g. of N-methyl-1,3-oxazino(5,6-c)rifamycin (prepared according to Examples 14 and 15) 45 ml. of toluene and 1.2 g. of 1-amino-4-methyl-piperazine at 75°C.

After 10 minutes heating, the reaction mixture is cooled, taken up with 100 ml. chloroform, washed with water acidified with acetic acid and then with water. The dried organic phase is concentrated to dryness and the residue is recrystallized from acetone to give 5.8 g. of pure rifampicin.

EXAMPLE 17

A solution of 7.5 g. of N-methyl-1,3-oxazine(5,6-c)rifamycin (prepared according to Examples 14 and 15) in 50 ml. chloroform is treated with 4 g. triethylamine and 1.5 g. 1-amino-4-methylpiperazine and the mixture thus obtained is allowed to stand 24 hours under stirring. The pH is adjusted to 5 by diluted acetic acid and the solution is washed with water. The organic phase is dried with sodium sulfate, filtered, concentrated to dryness and the residue is taken up with 40 ml. acetone. After standing overnight at 0°C, the precipitate thus obtained is filtered and 7.2 g. of pure rifampicin (activity: 95.5%) are isolated.

What we claim is:

1. A process for the preparation of 3-iminomethyl derivatives of rifamycin SV of formula

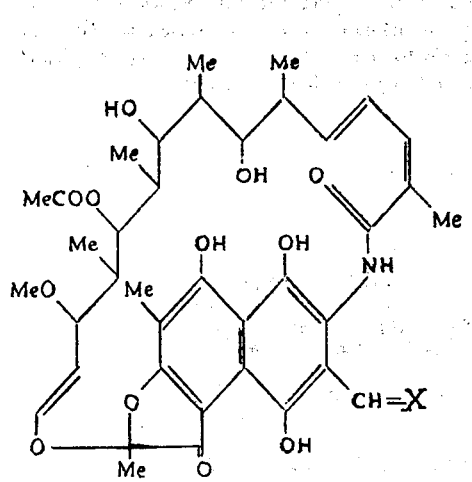

(III)

which comprises reacting rifamycin S of formula

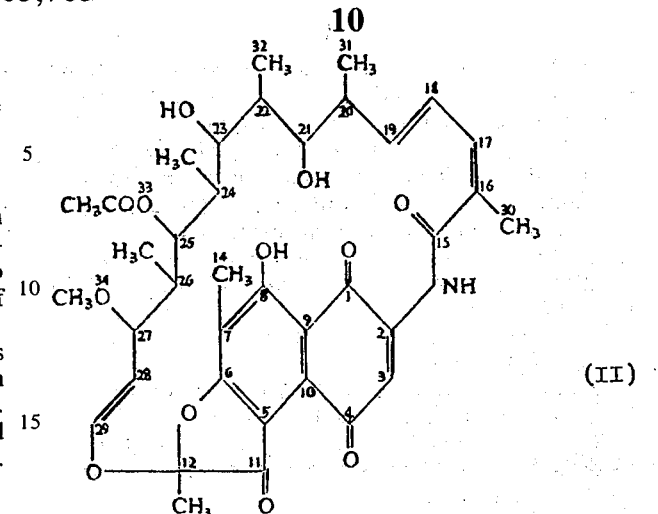

(II)

with a compound of formula

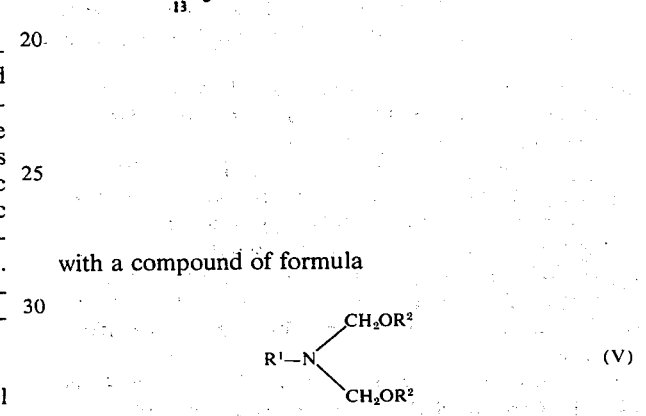

(V)

in which $R^1$ is lower alkyl, lower alkenyl, cycloalkyl having from 5 to 6 carbon atoms, phenyl, benzyl or $\alpha$- or $\beta$-phenethyl and $R^2$ is hydrogen or lower alkyl, in a first inert organic solvent at a temperature ranging from 0°C to the boiling temperature of the solvent to give a solution of 1,3-oxazino(5,6-c)rifamycins of formula (IV)

in which R¹ is as above defined, treating said solution with water and a second inert organic solvent immixible with water at a pH adjusted at a value from 4 to 6, then discharging the aqueous phase and treating the organic phase with a primary amine, hydrazine, mono-substituted hydrazine or asymmetric di-substituted hydrazine at a temperature from about 20°C to about 80°C under basic conditions, the derivatives (III) being finally isolated from the organic phase according usual techniques.

2. A process according to claim 1, wherein R¹ is t.butyl, methyl or allyl.

3. A process according to claim 1, wherein said first inert organic solvent is a dipolar aprotic solvent.

4. A process according to claim 3, wherein said dipolar aprotic solvent is dimethylsulfoxide, dimethylformamide or dimethylacetamide.

5. A process according to claim 1, wherein said second inert organic solvent are chlorinated or aromatic solvents.

6. A process according to claim 1, wherein said basic conditions are obtained by addition of a secondary or tertiary amine to the organic phase.

7. A process according to claim 6, wherein said secondary or tertiary amines are pyrrolidine, trimethylamine, triethylamine or 1-methyl-pyrrolidine.

8. A process according to claim 1, wherein said derivatives (III) are isolated from said organic phase by acidifying said phase to a pH from about 4 to about 5.5, washing with water, drying the phase and evaporating the solvent.

9. A process according to claim 1, wherein R¹ is t.butyl, methyl or allyl, said first inert organic solvent is dimethyl sulfoxide, dimethyl formamide or dimethyl acetamide, the temperature at which the compound of formula (II) is reacted with the compound of formula (V) is between about 15° and 100°C. said second inert organic solvent is methylene chloride or chloroform, said treatment of the organic phase being effected with 1-amino-4-methyl-piperazine substantially at room temperature, said basic conditions being obtained by adding pyrrolidine to the organic phase, the derivative isolated from this organic phase being rifampicin.

10. A process for the preparation of 3-iminomethyl derivatives of rifamycin SV of formula which comprises reacting rifamycin S of formula

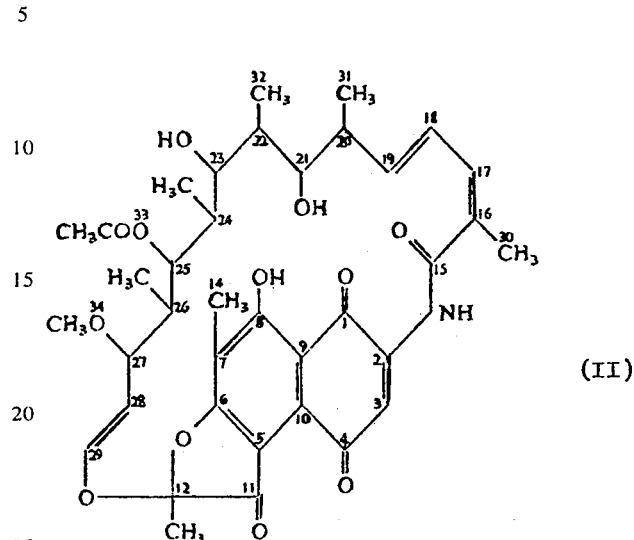

(II)

with a compound of formula

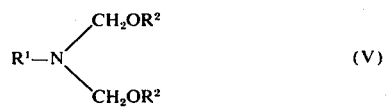

(V)

in which R¹ is lower alkyl, lower alkenyl, cycloalkyl having from 5 to 6 carbon atoms, phenyl, benzyl or α- or β-phenethyl and R² is hydrogen or lower alkyl, in a dipolar solvent at a temperature ranging from 15°C to 100°C to give a solution which is treated with water acidified at a pH from about 4 to about 6 to precipitate 1,3-oxazino(5,6-c)rifamycins of formula

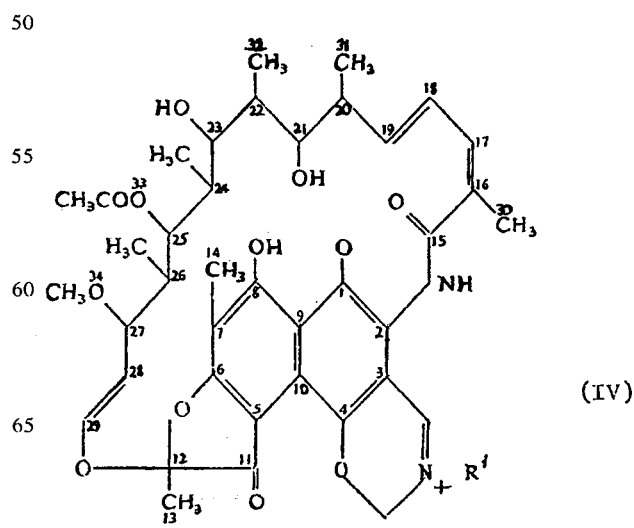

(IV)

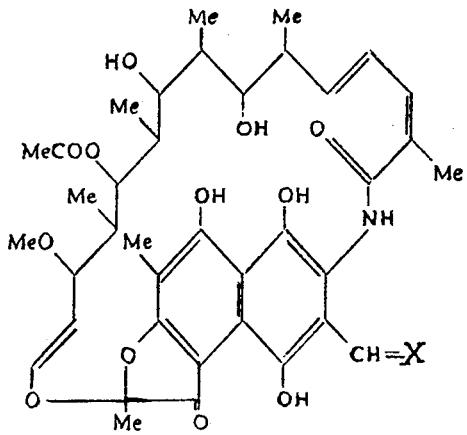

(III)

the 1,3-oxazino(5,6-c)rifamycins thus obtained being dissolved in an inert organic solvent and treated with a primary amine, hydrazine, mono-substituted hydrazine or asymmetric di-substituted hydrazine at a temperature from about 20°C to about 80°C under basic conditions, the derivatives (III) being finally isolated from the organic solution according to usual techniques.

* * * * *